(12) United States Patent
Walker et al.

(10) Patent No.: US 7,251,516 B2
(45) Date of Patent: Jul. 31, 2007

(54) NONINVASIVE GLUCOSE SENSOR

(75) Inventors: Stephen D. Walker, Boulder, CO (US);
Peter E. Nelson, Longmont, CO (US);
R. Dale Zellers, Lafayette, CO (US);
Charles W. Henry, Denver, CO (US);
John E. Repine, Englewood, CO (US)

(73) Assignee: Nostix LLC, Boulder, CO (US)

( * ) Notice: Subject to any disclaimer, the term of this patent is extended or adjusted under 35 U.S.C. 154(b) by 353 days.

(21) Appl. No.: 10/844,230

(22) Filed: May 11, 2004

(65) Prior Publication Data

US 2005/0256384 A1 Nov. 17, 2005

(51) Int. Cl.
*A61B 5/00* (2006.01)
(52) U.S. Cl. ....................................... 600/316
(58) Field of Classification Search ................ 600/316, 600/317, 322, 323
See application file for complete search history.

(56) References Cited

U.S. PATENT DOCUMENTS

| | | | |
|---|---|---|---|
| 4,805,623 A * | 2/1989 | Jobsis | 600/328 |
| 5,638,816 A * | 6/1997 | Kiani-Azarbayjany et al. | 600/316 |
| 5,817,010 A * | 10/1998 | Hibl | 600/344 |
| 6,424,850 B1 * | 7/2002 | Lambert et al. | 600/319 |
| 6,846,288 B2 * | 1/2005 | Nagar et al. | 600/437 |
| 2001/0034478 A1 * | 10/2001 | Lambert et al. | 600/318 |
| 2002/0106709 A1 * | 8/2002 | Potts et al. | 435/14 |
| 2004/0087843 A1 * | 5/2004 | Rice et al. | 600/319 |

* cited by examiner

*Primary Examiner*—Eric Winakur
*Assistant Examiner*—Etsub Berhanu
(74) *Attorney, Agent, or Firm*—Koestner Bortani LLP; Ken J. Koestner

(57) ABSTRACT

Glucose concentration is noninvasively measured by measuring a plurality of absorption values using at least one emitter operating at a corresponding plurality of emission wavelengths through a common optical sample volume and deriving glucose concentration from the absorption measurement values.

27 Claims, 4 Drawing Sheets

NONINVASIVE GLUCOSE SENSOR

BACKGROUND OF THE INVENTION

Diabetes is a disease in which the body does not properly produce or use insulin. Insulin is a hormone that converts sugar, starches and other food into energy for the body. The cause of diabetes is unknown, although both genetic and environmental factors such as obesity and lack of exercise are factors in determining disease development.

Approximately 17 million people in the United States, or 6.2% of the population, have diabetes. Diabetes is the fifth leading cause of death by disease in the United States. While an estimated 11.1 million people have been diagnosed, approximately 5.9 million people (35%) are unaware of affliction by the disease. (www.diabetes.org/info/diabetesinfo.jsp). Future incidence of diabetes is likely to increase, driven by an aging population, increasing incidence of obesity, and overall population growth.

Estimates for the worldwide incidence of diabetes vary greatly. One pharmaceutical industry research group report estimates approximately 135 million cases of diabetes in the world today, most undiagnosed, a number could rise to 300 million by 2025 (IMS Health, www.ims-global.com).

The three major types of diabetes are Type I, Type II, and gestational diabetes. Type I diabetes, also called juvenile diabetes, is usually diagnosed in children and young adults and results from the body's inability to produce insulin, the hormone that enables glucose to enter and fuel cells of the body. An estimated 10% of Americans who are diagnosed with diabetes have type I diabetes. Type II diabetes is the most common form and results from insulin resistance, the body's failure to properly use insulin, combined with relative insulin deficiency. Approximately 90% of Americans diagnosed with diabetes have type II diabetes. Glucose accumulates in the blood rather than entering cells, causing two problems, the immediate energy starvation of cells and long term high blood glucose levels that may permanently damage eyes, kidneys, nerves and/or heart. Pre-diabetes is a condition occurring when blood glucose levels are higher than normal but not insufficient to be type II diabetes. An estimated 16 million Americans have pre-diabetes. Gestational diabetes affects about 4% of all pregnant women, about 135,000 cases yearly in the United States.

Diabetes is often undiagnosed because many symptoms appear relatively harmless. Early detection and treatment can decrease the probability of developing the complications of diabetes.

For the people diagnosed with diabetes, the challenge is to actively and accurately manage diets and exercise programs, while also actively managing blood sugar to maintain glucose levels within an optimal range. The less aggressively blood sugar levels are managed, the higher the risk of development of one or more of the major secondary diseases. Diabetics have extra reason to be mindful of heart and blood vessel disease. Diabetes carries an increased risk for heart attack, stroke, and complications related to poor circulation. Two out of three people with diabetes die from heart disease and stroke. Diabetes is the leading cause of blindness among adults aged 21 to 74. Retinopathy develops in nearly all patients with poorly controlled type I diabetes and in more than 60% of patients with type II diabetes (Cefalu, W. T., Weir, G. C. Patient Care. September, 2003, p. 66). Diabetes accounts for 43% of end-stage renal disease. Kidney failure is treated only by dialysis and kidney transplantation to restore the kidney's blood-cleansing function. One common diabetes complication is diabetic neuropathy, damage to the nerves that run throughout the body, connecting the spinal cord to muscles, skin, blood vessels, and other organs. Up to 70% of people with diabetes suffer from mild to severe neuropathy, in many cases resulting in extremity amputations.

Direct medical and indirect expenditures attributable to diabetes are estimated at $132 billion annually. In 2002, direct medical expenditures alone totaled $91.8 billion including $23.2 billion for diabetes care, $24.6 billion for chronic complications resulting from diabetes; and $44.1 billion for excess prevalence of related medical conditions. Indirect expenditures resulting from lost workdays, restricted activity days, mortality, and permanent disability due to diabetes were estimated to total $39.8 billion. The total cost of diabetes treatment at $131.7 billion in 2002 exceeds the total 2002 cost for treating all forms of cancer, an estimated $107 billion. Some estimate that one of four Medicare dollars goes to diabetic healthcare costs.

"Diabetes imposes a substantial cost burden to society and, in particular, to those individuals with diabetes and their families. Eliminating or reducing the health problems caused by diabetes through factors such as better access to preventive care, more widespread diagnosis, more intensive disease management, and the advent of new medical technologies could significantly improve the quality of life for people with diabetes and their families while at the same time potentially reducing national expenditures for health care services and increasing productivity in the U.S. economy." (American Diabetes Association. "Economic Costs of Diabetes in the U.S. in 2002". *Diabetes Care* 26:917-932, 2003).

Normal blood glucose levels range between 80 and 120 milligrams/deciliter (mg/dl). For a person with diabetes, maintaining glucose levels within range can be difficult. Calories consumed cause blood sugar levels to rise due to the diabetic's inability or impairment in producing insulin. Accordingly, artificial insulin is to be taken via either a syringe, an insulin pump with an implanted catheter, or an oral medication to bring levels back into the target range. Even with vigilant management, blood sugar levels can drop below the optimal range while sleeping. Many diabetics are awakened at least once in the middle of the night to take a blood glucose measurement.

A blood glucose measurement commonly involves usage of a lancet to prick the skin, a test strip to collect the blood sample, and a glucometer to generate a reading. A typical diabetic tests blood glucose levels an estimated six times per day in a painful and costly process that is difficult to discretely execute in public settings. Should the measurement indicate levels are outside of the optimal range, then either insulin or calories are taken for appropriate correction.

SUMMARY

Glucose concentration is noninvasively measured by measuring a plurality of absorption values using at least one emitter operating at a corresponding plurality of emission wavelengths through a common optical sample volume and deriving glucose concentration from the absorption measurement values.

BRIEF DESCRIPTION OF THE DRAWINGS

Embodiments of the invention relating to both structure and method of operation, may best be understood by referring to the following description and accompanying drawings.

DETAILED DESCRIPTION

Diabetics have long sought a convenient, noninvasive glucose sensor that accurately measures blood sugar, substantially aiding the diabetic and physician in managing the diabetic condition. Near infrared spectrometry is an optical method that generally is used to measure light in a wavelength range from approximately 700-1300 nanometers (nm), and can be used to noninvasively determine glucose level in tissue.

In various embodiments, a diagnostic apparatus can continuously and noninvasively measure glucose levels in tissue. An emitter, in some embodiments a vertical cavity surface emitting laser (VCSEL) or semiconductor laser diode emitter, illuminates a single optical sample volume in tissue. A photo detector positioned nearby on the skin measures light absorption (A) through the optical sample volume. In some embodiments, temperature of the emitter is changed slightly, resulting in a small shift, for example 1-2 nanometers, in the emitted wavelength. Absorption is measured at the second temperature. Glucose concentration in the optical sample volume is determined from the two absorption measurements and the absorption factors of glucose and water.

What is desired is a device that can continuously and noninvasively monitor blood glucose levels.

A noninvasive glucose sensor is described that can be configured, for example, as a small device, attached to a wristband, that people with diabetes can wear to generate continuous and noninvasive measurements of blood glucose levels. The illustrative sensor and sensing technique enable measurement of glucose, water, and albumin noninvasively and continuously. The illustrative sensor can be implemented as a low power, small size, and low cost device.

A vertical cavity surface-emitting laser (VCSEL) is a type of semiconductor laser that can be configured as a tunable emitter. In some embodiments, the emitter can be used in a sensor for monitoring blood glucose levels. In alternative embodiments, edge-emitting semiconductor lasers can be configured as an emitter, typically for usage in glucose monitoring of mammals or plants. Generally, edge-emitting semiconductor lasers have less accuracy and may be less expensive than VCSELs.

In some embodiments, the noninvasive glucose sensor can be used with a responsive insulin delivery system to reduce or minimize deviations in glucose levels and consequences resulting from uncontrolled glucose levels.

Figure 1:
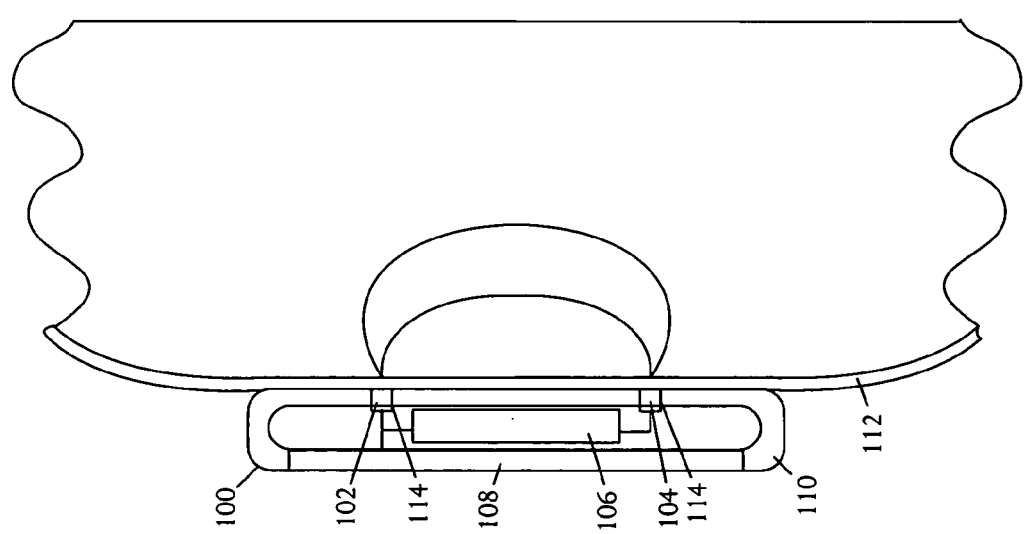
FIG. 1 is a schematic pictorial diagram illustrating an embodiment of a glucose sensor capable of noninvasive sensing of glucose and water.

Referring to FIG. 1, a schematic pictorial diagram illustrates an embodiment of a glucose sensor 100 capable of noninvasive sensing of glucose and water. The noninvasive glucose sensor 100 comprises at least one emitter 102, and at least one photo detector 104 configured to detect emissions from the emitter 102. The emitter 102 illuminates tissue with narrowband light. Some photons are reflected onto the detector 104. For illumination of 980 nanometer light, for example, glucose and water account for the majority of light absorbed in the tissue.

A controller 106 is coupled to the one or more emitters 102 and is adapted to control signal acquisition by the emitters 102 by shifting emitter wavelength to enable measurement of absorption at a plurality of wavelengths and derive a glucose concentration measurement from the absorption measurement values. The sensor 100 further comprises an interface 108 coupled to the controller 106 that exhibits a condition based on the glucose concentration measurement.

The glucose sensor 100 can be attached to a diabetic's arm using a device such as a flexible strap or band 112. The sensor 100 includes a semiconductor laser emitter 102, the photo detector 104, and various components such as electronic components. In an illustrative embodiment, the distance between the emitter 102 and the photo detector 104 can be approximately 3 centimeters. The emitter 102 injects photons through the skin into muscle tissue. The path of the photons is random due to scattering by reflective objects such as mitochondria. Photons that travel from the emitter 102 to the detector 104 travel through a roughly banana-shaped pathway forming an optical sample volume. Light absorption $A_{\lambda 1}$ through the optical sample volume at wavelength $\lambda_1$ is measured at a first emitter temperature. The emitter temperature is changed slightly by increasing or decreasing the drive current by 30-50%, resulting in a shift of 1-2 nm in emitter wavelength. Absorption $A_{\lambda 2}$ is measured at a second emitter wavelength $\lambda_2$. Glucose and water levels of the optical sample volume are determined from the two absorption measurements and the absorption factors of glucose and water according to equations (1) and (2):

$$A_{\lambda 1} = \epsilon_{\lambda 1}^G G + \epsilon_{\lambda 1}^W W \tag{1}$$

$$A_{\lambda 2} = \epsilon_{\lambda 2}^G G + \epsilon_{\lambda 2}^W W \tag{2}$$

where A is the absorption measured by a photo detector at a specific wavelength $\lambda$, G is glucose concentration, W is water concentration, $\epsilon_\lambda^G$ is the absorption factor for glucose at wavelength $\lambda$ and $\epsilon_\lambda^W$ is the absorption factor for water at wavelength $\lambda$. Solving for G and W yields equations (3) and (4):

$$G = \frac{\epsilon_{\lambda 2}^W A_{\lambda 1} - \epsilon_{\lambda 1}^W A_{\lambda 2}}{\epsilon_{\lambda 1}^G \epsilon_{\lambda 2}^W - \epsilon_{\lambda 1}^W \epsilon_{\lambda 2}^G} \tag{3}$$

$$W = \frac{\epsilon_{\lambda 1}^G A_{\lambda 2} - \epsilon_{\lambda 2}^G A_{\lambda 1}}{\epsilon_{\lambda 1}^G \epsilon_{\lambda 2}^W - \epsilon_{\lambda 2}^G \epsilon_{\lambda 1}^W}. \tag{4}$$

In some embodiments, the sensor 100 can also include a housing 110 that encloses the emitters 102, photo detector 104, and the controller 106, and has apertures 114 through which the emitters 102 and photo detectors 104 extend, enabling contact exterior to the housing 110. The sensor 100 may also include a band 112 coupled to the housing 110 and capable of mounting the housing 110 to a measurement body part. In a particular example, the sensor 100 may be configured for fastening to a person's wrist so that the band 112 may be a wrist band.

The sensor 100 can be battery-powered and sufficiently small in size to reduce or eliminate discomfort to the wearer.

Various types of emitters 102 may be used. In some embodiments, the emitter or emitters 102 can be vertical cavity surface emitting laser (VCSEL) elements. A VCSEL 102 emits narrowband light in a specified wavelength range that passes through body tissue in an interrogated body part. The photo detector 104 is mounted on the skin a short distance from the VCSEL emitter 102 and receives a signal indicative of analyte absorption in the tissue.

In one operating mode, the controller 106 controls the VCSEL emitter 102 to shift the emitter wavelength, enabling sampling of absorption at multiple wavelengths. VCSEL emitters 102 may be selected based on wavelengths that are most suitable for measuring particular a particular analyte or analytes. The controller 106 can use various techniques to control center wavelength of the VCSEL emitter 102. For example, the controller 106 can increase VCSEL drive current to change the center wavelength. Although the selected VCSEL wavelength may be within a range sensitive to glucose, typically the VCSELs 102 that are most suitable for glucose measurement are in a range from 700 to 1100 nanometers, and the wavelength is shifted in wavelength by ones or tens of nanometers to acquire multiple samples.

In a specific embodiment, a VCSEL 102 is selected that generates narrowband light in a range from 1055 to 1065 nanometers, and the controller 106 shifts the emitter wavelength by one or more nanometers for multiple measurements. In one example of operation in the first mode, narrowband light from a single VCSEL 102 in the 1055 to 1065 nm range is directed through a subject body part. The photo detector 104 is mounted on the skin a short distance away from the VCSEL emitter 102. Absorption (A1) by glucose and water in the tissue is measured at wavelength 1 ($\lambda 1$). The VCSEL emitter wavelength is shifted longer by more than one nanometer to wavelength 2 ($\lambda 2$) by increasing the VCSEL drive current and absorption 2 (A2) is measured. The multiple measurements result in two independent equations with two unknown analyte concentrations, for example glucose (G) and water (W). The equations are of the form:

$$A = \epsilon G + \epsilon W,$$

where $\epsilon$ is the absorption factor of the appropriate analyte at the emitted wavelength.

Usage of a single sensor 102, 104 enables acquisition of measurements in a single optical sample volume, thereby improving accuracy by eliminating even slight physiological differences in samples.

In some sensors 100, the interface 108 can be a visual display that is coupled to the controller 106 and can present a visible display of the condition based on the glucose concentration measurement. Some sensors 100 may use an audio alarm or annunciator that can be activated by the controller 106 to generate an audible signal indicative of the condition based on glucose concentration. Some glucose sensors 100 may have multiple interfaces 108 for example, including one or more visual displays and one or more audio alarms. In other embodiments, other types of annunciators or signaling devices can be used, that can produce audible, visual, vibration, or electronic signals, or a combination of signals.

The controller 106 may be configured to selectively generate an alarm signal based on a particular condition or conditions. For example, the controller 106 can automatically annunciate an alarm in response to measured glucose levels decreasing below a predetermined lower glucose concentration limit or to glucose concentrations increasing to above a predetermined upper glucose concentration limit. Alternatively, the controller 106 can cause automatic annunciation of an alarm signal for measured water concentrations decreasing below a lower water concentration level or increasing above an upper water concentration level.

In various embodiments, the emitter or emitters 102 can be vertical cavity surface-emitting lasers (VCSEL), edge-emitting semiconductor lasers, and the like.

The illustrative measurement apparatus and associated operating method can be used as a diagnostic test capable of replacing a conventional glucose tolerance test and capable of usage in detecting heart disease in an exercising individual. The illustrative techniques and devices can also be used to detect various patient conditions that are associated with a decreased concentration in cerebral spinal fluid (CSF) including bacterial meningitis, hypoglycemic seizures, coma, sleep disorders, stupor, and others. The depicted apparatus and associated operating method can also be used in combination with insulin administration to lower glucose levels. In a similar but complementary usage, the apparatus and method can be used with a responsive glucose or glycogen administration device or system to raise glucose levels. Glucose levels can increase in diabetics as a consequence of stress, infection, or other non-diabetic conditions.

The depicted apparatus and associated operating method can also be used in combination with insulin administration to lower glucose levels. In a similar but complementary usage, the apparatus and method can be used with a responsive glucose or glycogen administration device or system to raise glucose levels. Glucose levels can increase in diabetics as a consequence of stress, infection, or other non-diabetic conditions.

In an illustrative embodiment, the apparatus can measure blood glucose at a selected sample rate. In a particular example, the apparatus can be configured or controlled to measure blood glucose continuously every 100 msec, a rate that enables early trend analysis and real-time analysis of changes in glucose. In contrast, standard glucose monitoring devices produce a single measurement which does not information the diabetic whether the glucose level is increasing or decreasing at a particular moment. Conventional glucose measurement devices can activate an alarm based on a comparison of the single measurement with a preset threshold value. However a trend analysis capability of the illustrative device and method may be more accurate and enable prediction of a diagnostic condition of interest prior to a threshold value being exceeded. Consequently, trend analysis may enable earlier treatment with insulin or glucose to reduce swings in glucose level.

Figure 2:
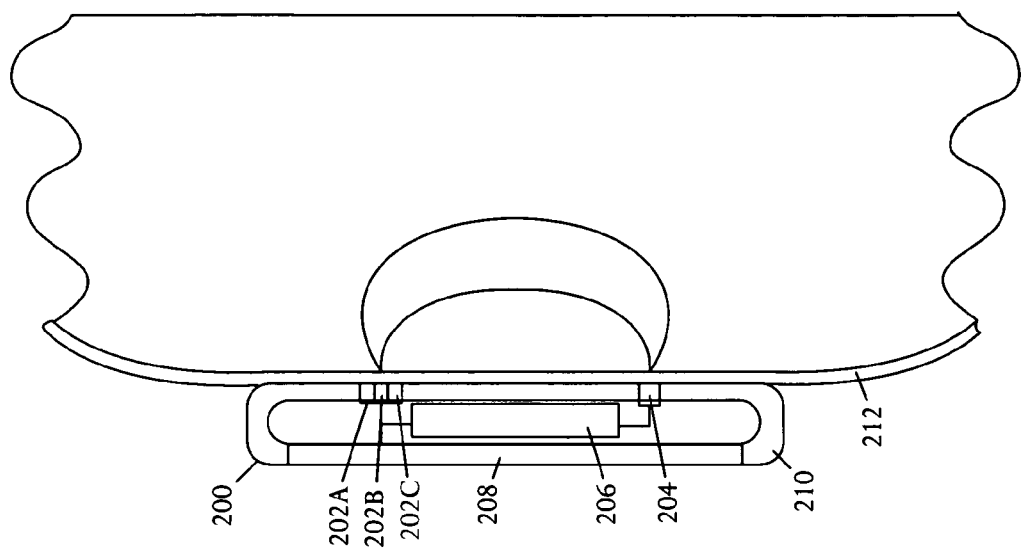
FIG. 2 is a schematic pictorial diagram illustrating another embodiment of a noninvasive glucose sensor in a device that includes a plurality of vertical cavity surface emitting lasers (VCSELs).

Referring to FIG. 2, a schematic pictorial diagram illustrates another embodiment of a noninvasive glucose sensor 200 that comprises a plurality of vertical cavity surface emitting lasers (VCSELs) 202A, 202B, and 202C, or other suitable emitters. The VCSELs 202A, 202B, and 202C include an emitter with a selected center wavelength with the plurality of VCSELs including individual VCSELs with multiple different emitter center wavelengths. The glucose sensor 200 further comprises at least one photo detector 204 configured to detect emissions from the VCSELs 202A, 202B, and 202C. In the illustrative embodiment, the sensor 200 includes three VCSELs 202A, 202B, and 202C and one photo detector 204. In other embodiments, the sensor may have multiple photo detectors so that each VCSEL emitter is associated with a photo detector. In other embodiments, the sensor 200 may include more VCSELs or fewer VCSELs, or may include more photo detectors or fewer photo detectors. In some embodiments, the number of VCSEIs may differ from the number of photo detectors. In the illustrative example, a sensor with multiple VCSELs may have only a single photo detector so that the usage of the photo detector may be time multiplexed.

The glucose sensor 200 further comprises a controller 206 coupled to the plurality of VCSELs 202A, 202B, and 202C and adapted to control signal acquisition by the VCSELs including activating VCSELS that operate at multiple center wavelengths to measure absorption at corresponding multiple wavelengths. From the multiple different wavelength samples, the controller 206 derives a glucose concentration measurement from the absorption measurement values.

The glucose sensor 200 also comprises an interface 208, such as a display, alarm, or both, coupled to the controller that exhibits a condition based on the glucose concentration measurement.

In some embodiments, the sensor 200 can also include a housing 210 enclosing the VCSELs 202A, 202B, and 202C, photo detector 204, and the controller 206. The sensor 200 may also include a band 212 coupled to the housing 210 and capable of mounting the housing 210 to a measurement body part.

In a specific embodiment, the VCSELs 202A, 202B, and 202C are selected that generate narrowband light in a range from 700 to 1100 nanometers. For example one VCSEL 202A may have a center wavelength of 1060 nm, another VCSEL 202B may have a center wavelength of 980 nm, and a third VCSEL 202C may have a center wavelength of 850 nm. The controller 208 typically activates the VCSELs 202A, 202B, and 202C individually at different times, although in some embodiments operation may be feasible when the VCSELs emit simultaneously. In one example of operation in the first mode, narrowband light from the first VCSEL 202A at the center wavelength of 1060 nm is directed through a subject body part. A photo detector 204 is mounted on the skin a short distance away from the VCSEL emitters 202A, 202B, and 202C. Absorption ($A1_{1060}$) by glucose and water in the tissue are measured at wavelength 1 ($\lambda1=1060$ nm) emitted by VCSEL 202A. Absorption ($A2_{1060}$) is measured a few milliseconds later at a wavelength of $\lambda1+\Delta$ nanometers, where $\Delta$ is typically about 1-2 nm. The controller 206 activates each VCSEL emitter in turn and measures two absorptions, 1-2 nm apart. The multiple measurements result in two independent equations with two unknown analyte concentrations, for example glucose (G) and water (W). The equations are of the form:

$$A = \epsilon G + \epsilon W,$$

where $\epsilon$ is the absorption factor of the appropriate analyte at the emitted wavelength.

Figure 3:
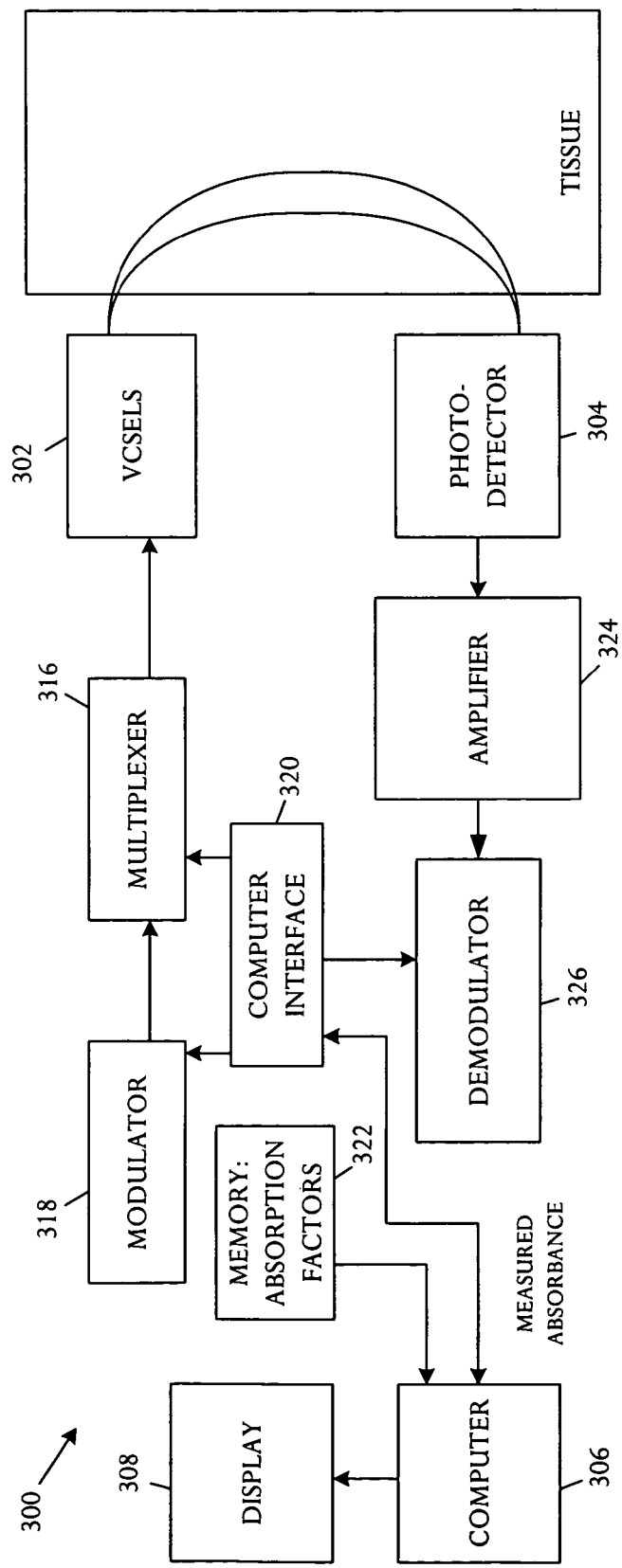
FIG. 3 is a schematic block diagram showing an embodiment of a near-infrared sensor (NIRS) that is capable of continuous and noninvasive monitoring of blood glucose levels.

Referring to FIG. 3, a schematic block diagram illustrates an embodiment of a near-infrared sensor (NIRS) 300 that is capable of continuous and noninvasive monitoring of blood glucose levels, as well as levels of other analytes. Sensor elements of the near-infrared sensor 300 are Vertical-Cavity Surface-Emitting Laser (VCSEL) emitters 302 that operate in combination with photo detectors 304 to enable measurement of absorption in tissue of various analytes. VCSELs 302 are a form of laser diode that have intrinsic characteristics superior to edge-emitter lasers in terms manufacturing, compact low-cost packaging, and spectral stability. In contrast to edge-emitter lasers that are several hundred microns long and emit light in the plane of a laser chip, VCSELs are circular in shape and have a small size, for example in the range of about 10 μm in diameter, and emit perpendicular to the plane of the chip, facilitating access to the emitted light beam. VCSELs are manufactured using standard gallium-arsenide (GaAs) processing techniques and the emitted beams are circular, low-divergence, and substantially aberration free. A fabricated VCSEL is a nearly planar structure which can be tested while remaining on an integrated circuit wafer by completely automated techniques, thereby reducing laser cost. Operating currents are typically in the range of 5-25 milliamps, compared to 30-100 milliamps in an edge-emitting laser. Power supplied to the VCSEL-based sensor is therefore much lower than power to an edge-emitting laser-based sensor, a characteristic that is valuable for hand-held, battery-operated instruments that include laser technology.

Accurate implementation of the emitter wavelength in all lasers in a near infrared sensor translates into higher measurement accuracy. Emission wavelength of a VCSEL is determined by the average thickness and composition of semiconductor layers. The emission wavelength of a VCSEL generally remains substantially constant throughout the useful lifetime of the VCSEL. In contrast, wavelengths for edge-emitter lasers migrate during aging so that even for edge-emitter lasers with a wavelength characteristic that is widely known at the time of manufacture, a substantial uncertainty in actual wavelength characteristic results as the laser ages.

An emission pathway for the near-infrared sensor 300 also includes a multiplexer 316 and a modulator 318. The modulator 318 is used in the sensor 300 to perform high-frequency intensity modulation on the optical beam produced by the VSEL emitter 302. The modulator 318 is used to controllably vary VCSEL current, varying the emitter wavelength to enable wavelength shifting. In a particular embodiment, the modulator 318 is used to increase wavelength by one or more nanometers to direct measurements to particular analytes. In a near-infrared sensor 300 that is useful for measuring glucose or water concentration, the center wavelength is approximately 980 nm and the modulator 318 shifts wavelength by one or two nanometers. Multiplexer 318 is used in the sensor 300 to perform high-frequency intensity modulation on the optical beam produced by the VCSEL 302.

A photo detection pathway in the NIRS sensor 300 includes a photo detector 304, an amplifier 324, and a demodulator 326. In a particular embodiment, the photo detector 304 is a silicon avalanche photodiode; although other types of photo detectors may be used. Silicon avalanche diodes are highly suitable on the basis of high quantum efficiency, for example 19%, at 980 nanometers, resulting in a photo sensitivity of 0.5 A/W. The amplifier 324 is positioned between the photo detector 304 and the demodulator 326 to amplify the signals. One example of a suitable amplifier 324 is a preamplifier followed in series by an amplifier. The demodulator 326 is used to quantify absorption. Strength of absorption is proportional to the change in modulation amplitude.

A computer interface block 320 initiates an absorption measurement at a selected first wavelength $\lambda1$, then switches the VCSEL center wavelength for subsequent measurements. In embodiments with multiple VCSELs having different center wavelengths, the computer interface block 320 initiates a measurement at each of the VCSELs. In embodiments using a single VCSEL to generate multiple wavelengths, the computer interface block 320 initiates the first wavelength λ1 for a selected time interval, for example about 100 milliseconds, then switches the VCSEL to a second wavelength λ2 and subsequent wavelengths, if desired. In a particular embodiment, the second wavelength λ2 may shift the wavelength, for example by increasing one or more nanometers in wavelength, for a selected time, then shift one or two nanometers again to produce a third wavelength λ3. The computer interface block 320 also labels absorption values for the computer 306.

The computer 306 computes analyte concentrations, for example glucose and water, from absorption at the different wavelengths, using absorption factors stored in a memory 322. The individual analytes have corresponding absorption factors at the different wavelength that are selected and stored in the memory 322.

The computer 306 performs the computations to derive concentrations of various analytes, for example glucose and water, and displays the results in a suitable manner via a display 308. The display 308 may be any type of visual, audio, or other type of display that conveys desired information. For example, the display 308 can be a visual screen that includes characters indicative of a condition based on analyte concentration values. In other examples, the display 308 may simply be an annunciator or alarm that sounds when an analyte level falls below or rises above a particular preset value. In some embodiments, the display 308 may be a warning light, such as a light-emitting diode.

The various functions, processes, methods, and operations performed or executed by the system can be implemented as programs that are executable on various types of processors, controllers, central processing units, microprocessors, digital signal processors, state machines, programmable logic arrays, and the like. The programs can be stored on any computer-readable medium for use by or in connection with any computer-related system or method. A computer-readable medium is an electronic, magnetic, optical, or other physical device or means that can contain or store a computer program for use by or in connection with a computer-related system, method, process, or procedure. Programs can be embodied in a computer-readable medium for use by or in connection with an instruction execution system, device, component, element, or apparatus, such as a system based on a computer or processor, or other system that can fetch instructions from an instruction memory or storage of any appropriate type. A computer-readable medium can be any structure, device, component, product, or other means that can store, communicate, propagate, or transport the program for use by or in connection with the instruction execution system, apparatus, or device.

The illustrative block diagrams and flow charts depict process steps or blocks that may represent modules, segments, or portions of code that include one or more executable instructions for implementing specific logical functions or steps in the process. Although the particular examples illustrate specific process steps or acts, many alternative implementations are possible and commonly made by simple design choice. Acts and steps may be executed in different order from the specific description herein, based on considerations of function, purpose, conformance to standard, legacy structure, and the like.

Figure 4A:
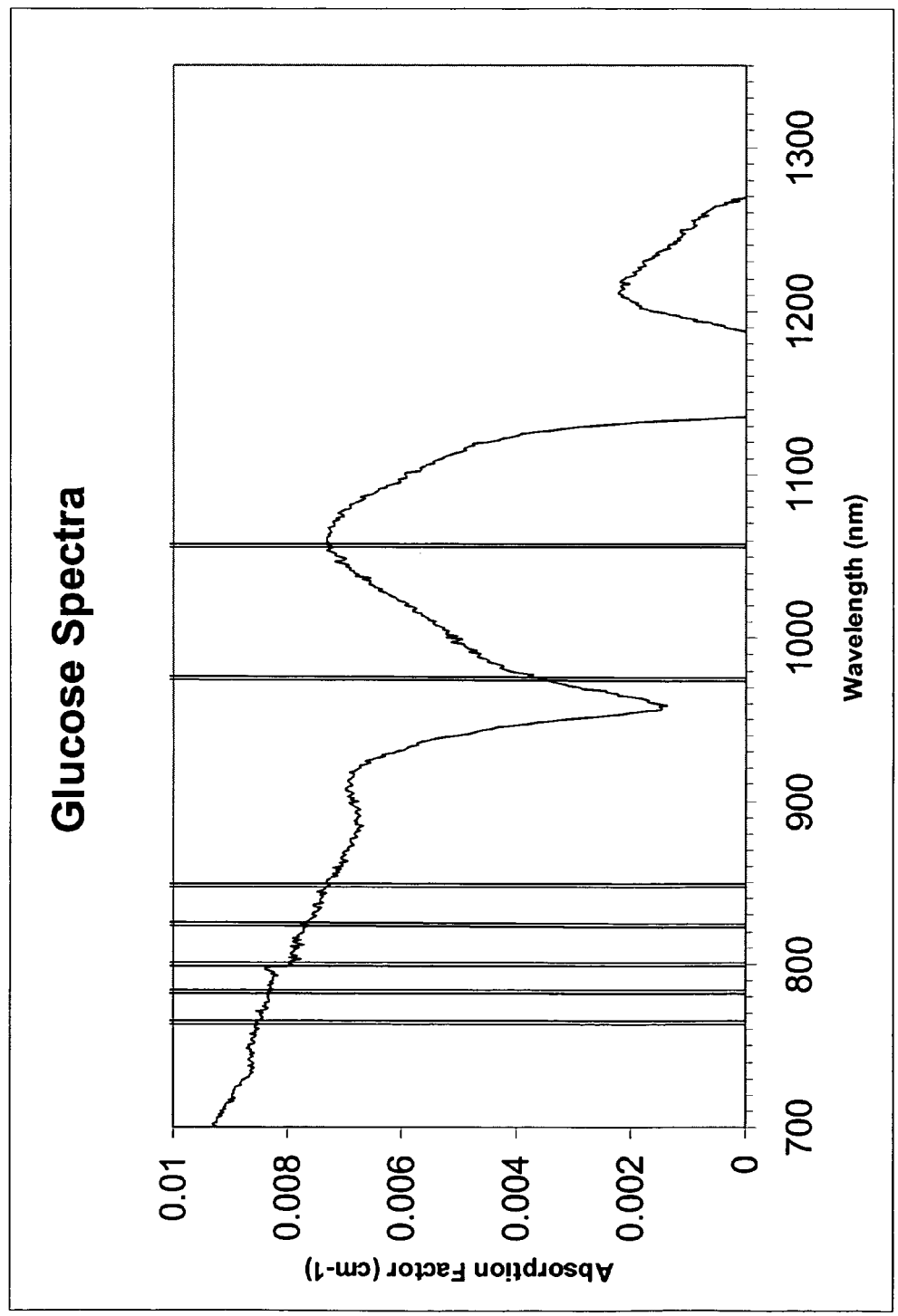
FIG. 4A is a graph showing spectra of glucose absorption in the 700-1100 nanometer wavelength range with paired lines representing specific wavelengths at which the glucose concentration may be measured with sensors including VCSEL emitters and silicon detectors.

Absorption factor, expressed per centimeter, is the amount of light at a specific wavelength that an analyte absorbs light. Examples of analytes include glucose, water, and hemoglobin. Absorption factor for glucose is most significant in the near infrared (NIR) range of 700-1100 nm shown in a glucose spectra graph depicted in FIG. 4A. FIG. 4 also relates to a method and apparatus embodiment with seven wavelength spectra pairs indicating wavelengths at which glucose can be most efficiently measured based on a technical capability to make measurements. For example, a vertical cavity surface emitter laser (VCSEL) with optical power greater than 4 milliwatts (mW) is available at the wavelengths. VCSELs with sufficient power can be fabricated only at particular wavelengths determined by quantum bands of the laser cavity material. In alternative embodiments, an avalanche photodiode (APD) detector with optical sensitivity greater than 0.5 A/W is available at the wavelengths. Silicon APDs can function as a detector material with sufficient photosensitivity in the NIR range to enable usage in detecting analytes.

Figure 4B:
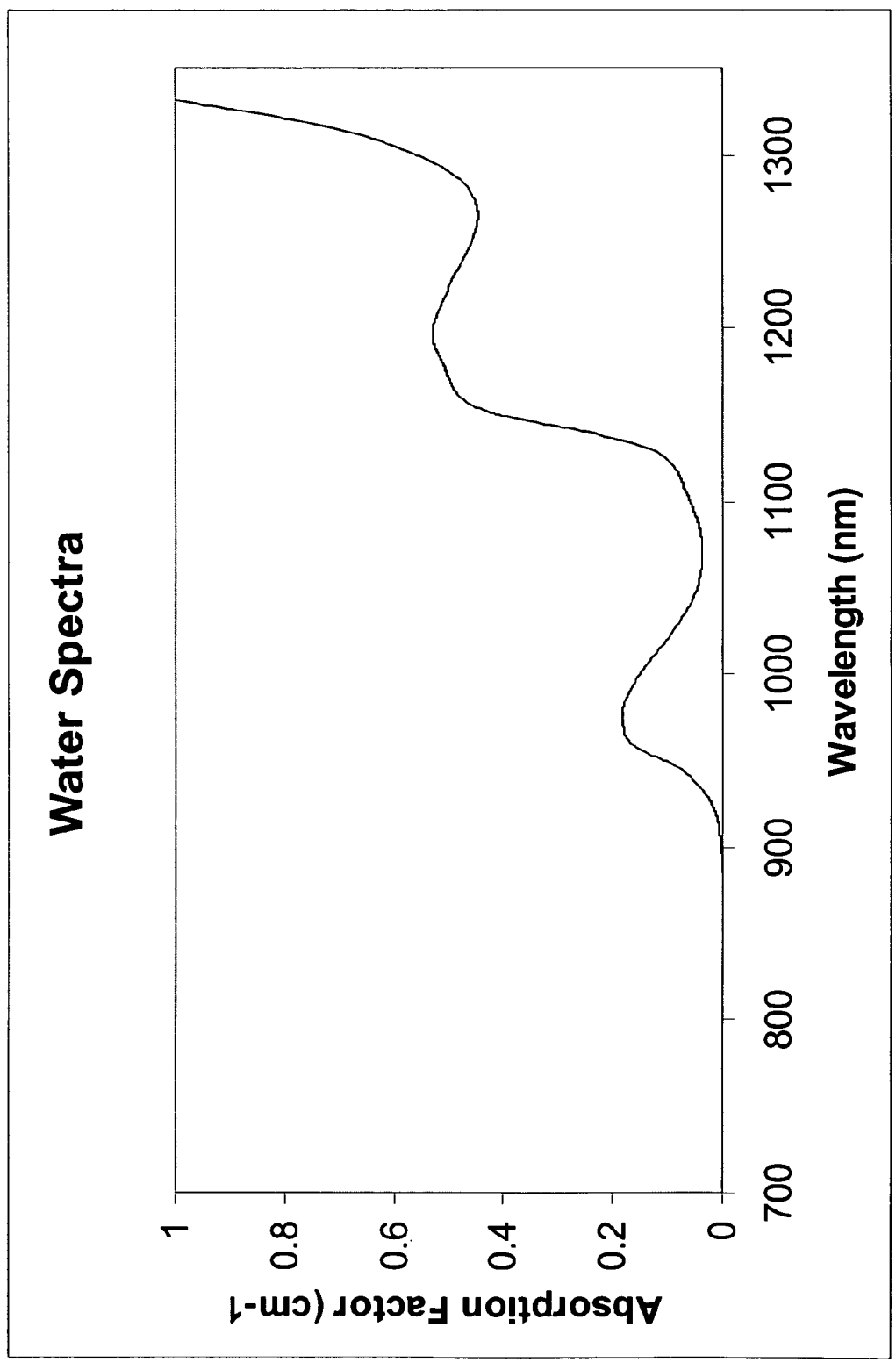
FIG. 4B is a graph depicting spectra of water absorption in the 700-1100 nanometer (nm) wavelength range and showing that the absorption factor of water is fifty times that of glucose at 980 nm but only 7.5 times larger at 1060 nm, a useful wavelength for measuring glucose absorption.

Another analyte with significant absorption factor in the NIR range and a high concentration is water, as is shown in a water spectra graph depicted in FIG. 4B. The ratio between oxygenated hemoglobin and deoxyhemoglobin varies with respiration in the 700-850 nm wavelength range. Although fat, albumin, and collagen absorb NIR light, concentrations do not vary rapidly in the manner of water and glucose in diabetics. Most changes in overall light absorption in tissue results from presence of water and glucose. Glucose concentration can be sensed optimally at a wavelength of approximately 1060 nm because the water absorption factor is 7.5 times larger than glucose. At 980 nm, the water absorption factor is fifty times larger than the glucose absorption factor. At 765 nm, 780 nm, 800 nm, 825 nm, and 850 nm, variation of light absorption by oxygenated hemoglobin and deoxyhemoglobin has significant interference.

A configuration including a single emitter operating through a single optical sample volume reduces or eliminates water interference in the glucose measurement. Water comprises 60-80% of tissue and has strong light absorption at the same wavelengths in the spectra as glucose.

The single optical sample volume measurement has several attributes. Two light absorption measurements are acquired through the same optical sample volume to determine both glucose and water components. Total absorption in the optical sample volume is composed of glucose and water in blood, interstitial fluid, and intracellular fluid. The percentage of each fluid component is different between two optical sample volumes. Light lost to scattering is identical between two absorption measurements taken through the same optical sample volume.

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. For example, the illustrative embodiments show particular arrangements of emitters and detectors. Many other arrangements are possible including either single or multiple emitters and/or sensors. The number of emitters may be one or more, and may be larger than two. The system may have a single detector or multiple detectors. The number of detectors and emitters may be the same or different. Furthermore, although a particular center wavelength is disclosed for the illustrative embodiments, for various applications other wavelengths may be used. Also, the illustrative sensors are shown as devices for mounting on a person's wrist. In other embodiments, the sensors may be arranged for attachment on any other locations on the body.

What is claimed is:

1. A noninvasive glucose sensor comprising:
at least one emitter;
at least one photo detector configured to detect emissions from the emitter;
a controller coupled to the at least one emitter adapted to control infrared emission by the emitter including shifting of emitter wavelength to measure absorption at a plurality of wavelengths through a common optical sample volume, and deriving a glucose concentration measurement from measured absorption values wherein:
the controller controls the at least one emitter to shift emitter wavelength by at least one nanometer between two measurement samples in a range from ±5 nm from a selected center wavelength, resulting in two independent equations with two unknown concentrations of analytes glucose (G) and water (W) the equations being of the form:

$$A_{\lambda 1} = \epsilon_{\lambda 1}^G G + \epsilon_{\lambda 1}^W W$$

$$A_{\lambda 2} = \epsilon_{\lambda 2}^G G + \epsilon_{\lambda 2}^W W$$

where A is absorption and ε is absorption factor of an analyte at a wavelength, the controller solving the equations for glucose concentration (G) and water concentration (W) using equations of the form:

$$G = \frac{\epsilon_{\lambda 2}^W A_{\lambda 1} - \epsilon_{\lambda 1}^W A_{\lambda 2}}{\epsilon_{\lambda 1}^G \epsilon_{\lambda 2}^W - \epsilon_{\lambda 1}^W \epsilon_{\lambda 2}^G}$$

$$W = \frac{\epsilon_{\lambda 1}^G A_{\lambda 2} - \epsilon_{\lambda 2}^G A_{\lambda 1}}{\epsilon_{\lambda 1}^G \epsilon_{\lambda 2}^W - \epsilon_{\lambda 2}^G \epsilon_{\lambda 1}^W}.$$

2. The sensor according to claim 1 further comprising:
an alarm coupled to the controller that is annunciated automatically on one or more preselected conditions selected from among a group of conditions comprising: (1) glucose levels decreasing below a predetermined threshold, (2) glucose levels increasing above a predetermined threshold, (3) water levels decreasing below a predetermined threshold, and (4) water levels increasing above a predetermined threshold.

3. The sensor according to claim 1 wherein:
the at least one emitter is selected from among vertical cavity surface emitting laser (VCSEL) emitters and semiconductor laser diode emitters.

4. The sensor according to claim 1 wherein:
the controller is capable of generating an electronic signal indicative of a condition based on the glucose concentration measurement, the signal for actuating a syringe or pump to inject insulin.

5. The sensor according to claim 1 further comprising:
the at least one emitter configured for coupling to skin in a body-wearable arrangement; and
the at least one photo detector configured for coupling to the skin in the body-wearable arrangement.

6. The sensor according to claim 1 further comprising:
the controller configured to increase or decrease drive current to the at least one emitter to modify emitter temperature resulting in a shift in emitter wavelength, the glucose concentration in the common optical sample volume being determined from absorption measurements acquired at wavelengths differing by the wavelength shift.

7. The sensor according to claim 1 further comprising:
the controller configured to increase or decrease drive current to the at least one emitter to modify emitter temperature resulting in a shift of 1-2 nm in emitter wavelength, the glucose concentration in the common optical sample volume being determined from absorption measurements acquired at wavelengths differing by the 1-2 nm wavelength shift.

8. The sensor according to claim 1 further comprising:
an interface coupled to the controller that exhibits a condition based on the glucose concentration measurement.

9. The sensor according to claim 8 further comprising:
a visual display coupled to the controller capable of presenting a display of the condition based on the glucose concentration measurement visible to an individual upon which the measurement is taken.

10. The sensor according to claim 8 further comprising:
an annunciator coupled to the controller capable of generating a signal indicative of the condition based on the glucose concentration measurement, the signal being selected from among a group consisting of audible, visual, vibration, and electronic signals, or a combination thereof.

11. The sensor according to claim 1 further comprising:
a housing enclosing the at least one emitter, the at least one photo detector, and the controller, and having apertures for insertion of the emitter and photo detector enabling contact exterior to the housing; and
a band coupled to the housing and capable of mounting the housing to a measurement body part, the housing and band configured in the body-wearable arrangement.

12. The sensor according to claim 1 wherein:
the at least one emitter generates narrowband light that is shifted under control of the controller to a plurality of emitter wavelengths.

13. The sensor according to claim 1 wherein:
the at least one emitter generates narrowband light in a range from 760-1065 nm that is shifted in a range of ones to tens of nanometers under control of the controller to a plurality of emitter wavelengths.

14. The sensor according to claim 1 wherein:
the controller controls the at least one emitter to shift emitter wavelength by 1-2 nanometers between measurement samples for one or more wavelengths selected from a group of approximate wavelengths comprising 1060 nm, 980 nm, 850 nm, 825 nm, 800 nm, 780 nm, and 765 nm.

15. A noninvasive glucose sensor comprising:
a plurality of emitters capable of generating multiple-wavelength emissions at multiple different emitter center wavelengths;
at least one photo detector configured to detect emissions from the emitters;
a controller coupled to the plurality of emitters and adapted to control signal acquisition by the emitters including activating ones of the plurality of emitters operating at multiple wavelengths to measure absorption at corresponding multiple wavelengths through a common optical sample volume, and deriving a glucose concentration measurement from the absorption measurement values, wherein:

the controller controls the emitters sequentially to shift emitter wavelength by at least one nanometer between two measurement samples in a range from ±5 nm from a selected center wavelength, resulting in two independent equations with two unknown concentrations of analytes glucose (G) and water (W) the equations being of the form:

$A_{\lambda 1} = \epsilon_{\lambda 1}^{G} G$ (Center Wavelength)$+\epsilon_{\lambda 1}^{W} W$ (Center Wavelength)

$A_{\lambda 2} = \epsilon_{\lambda 2}^{G} G$ (Center Wavelength)$+\epsilon_{\lambda 2}^{W} W$ (Center Wavelength)

where A is absorption and e is absorption factor of an analyte at a wavelength, the controller solving the equations for glucose concentration (G (Center-Wavelength)) and water concentration (W (Center Wavelength)) using equations of the form:

$$G(CenterWavelength) = \frac{\varepsilon_{\lambda 2}^{W} A_{\lambda 1} - \varepsilon_{\lambda 1}^{W} A_{\lambda 2}}{\varepsilon_{\lambda 1}^{G} \varepsilon_{\lambda 2}^{W} - \varepsilon_{\lambda 1}^{W} \varepsilon_{\lambda 2}^{G}}$$

$$W(CenterWavelength) = \frac{\varepsilon_{\lambda 1}^{G} A_{\lambda 2} - \varepsilon_{\lambda 2}^{G} A_{\lambda 1}}{\varepsilon_{\lambda 1}^{G} \varepsilon_{\lambda 2}^{W} - \varepsilon_{\lambda 2}^{G} \varepsilon_{\lambda 1}^{W}},$$

glucose (G) and water (W) concentrations being calculated using equations of the form:

$$G = \frac{G(CenterWavelength1) + G(CenterWavelength2) + \ldots}{n}$$

$$W = \frac{W(CenterWavelength1) + W(CenterWavelength2) + \ldots}{n}$$

where n is the number of emitters.

16. The sensor according to claim 15 further comprising: an alarm coupled to the controller that is annunciated automatically on one or more preselected conditions selected from among a group of conditions comprising: (1) glucose levels decreasing below a predetermined threshold, (2) glucose levels increasing above a predetermined threshold, (3) water levels decreasing below a predetermined threshold, and (4) water levels increasing above a predetermined threshold.

17. The sensor according to claim 15 wherein: the plurality of emitters is selected from among vertical cavity surface emitting laser (VCSEL) emitters and semiconductor laser diode emitters.

18. The sensor according to claim 15 wherein: the controller is capable of generating an electronic signal indicative of a condition based on the glucose concentration measurement, the signal for actuating a syringe or pump to inject insulin.

19. The sensor according to claim 15 further comprising: the plurality of emitters each configured for coupling to skin in a body-wearable arrangement; and the at least one photo detector configured for coupling to the skin in the body-wearable arrangement.

20. The sensor according to claim 15 further comprising: the controller having a capability to increase or decrease drive current to the plurality of emitters to modify emitter temperature resulting in a shift in emitter wavelength, the glucose concentration in the common optical sample volume being determined from absorption measurements acquired at wavelengths differing by the wavelength shift.

21. The sensor according to claim 15 further comprising: an interface coupled to the controller that exhibits a condition based on the glucose concentration measurement.

22. The sensor according to claim 21 further comprising: a visual display coupled to the controller capable of presenting a display of the condition based on the glucose concentration measurement visible to an individual upon which the measurement is taken.

23. The sensor according to claim 21 further comprising: an annunciator coupled to the controller capable of generating an audible signal indicative of the condition based on the glucose concentration measurement.

24. The sensor according to claim 15 further comprising: a housing enclosing the plurality of emitters, the at least one photo detector, and the controller, and having apertures for insertion of the photo detectors enabling contact exterior to the housing; and a band coupled to the housing and capable of mounting the housing to a measurement body part, the housing and band configured in the body-wearable arrangement.

25. The sensor according to claim 15 wherein: the emitters generate narrowband light at the multiple emitter wavelengths.

26. The sensor according to claim 15 wherein: the plurality of emitters generate narrowband light in a range from 760-1065 nm including different wavelengths that vary in a range of ones to tens of nanometers.

27. The sensor according to claim 15 wherein: the controller controls the plurality of emitters to shift emitter wavelength by 1-2 nanometers between measurement samples for one or more wavelengths selected from a group of approximate wavelengths comprising 1060 nm, 980 nm, 850 nm, 825 nm, 800 nm, 780 nm, and 765 nm.

* * * * *